United States Patent [19]

Mahulikar et al.

[11] Patent Number: 4,748,136

[45] Date of Patent: May 31, 1988

[54] CERAMIC-GLASS-METAL COMPOSITE

[75] Inventors: Deepak Mahulikar, Meriden; Narendra N. SinghDeo, New Haven, both of Conn.

[73] Assignee: Olin Corporation, New Haven, Conn.

[21] Appl. No.: 924,968

[22] Filed: Oct. 30, 1986

[51] Int. Cl.[4] .............................................. C03C 14/00
[52] U.S. Cl. ........................................ 501/32; 501/53
[58] Field of Search ................................... 501/53, 32

[56] References Cited

U.S. PATENT DOCUMENTS

| | | | |
|---|---|---|---|
| 4,491,622 | 1/1985 | Butt | 428/632 |
| 4,524,238 | 6/1985 | Butt | 174/52 |
| 4,532,222 | 7/1985 | Butt | 501/32 |
| 4,569,692 | 2/1986 | Butt | 75/235 |
| 4,659,404 | 4/1987 | Butt | 156/62.2 |
| 4,682,414 | 7/1987 | Butt | 29/840 |
| 4,687,540 | 8/1987 | SinghDeo et al. | 156/630 |
| 4,696,851 | 9/1987 | Pryor | 428/210 |

Primary Examiner—William R. Dixon, Jr.
Assistant Examiner—David M. Brunsman
Attorney, Agent, or Firm—Gregory S. Rosenblatt; Paul Weinstein

[57] ABSTRACT

The present invention is directed to a composite and process of forming the composite comprising metallic particles for enhancing the flow characteristics of said composite, a glass for adhering the composite together and the balance essentially ceramic particles. The composite has a matrix comprising the glass with the ceramic and metallic particles dispersed therein. The metallic particles are preferably present in the composite at a volume percentage so as to be discontinuously dispersed throughout.

34 Claims, No Drawings

CERAMIC-GLASS-METAL COMPOSITE

While the invention is subject to a wide range of applications, it is especially suited for use in a broad range of applications incorporating electro-ceramics, engineering ceramics, optical ceramics and bio-ceramics. The invention discloses the bonding together of ceramic and metallic particles to form a coherent composite with desired properties which may be specifically tailored for specific applications such as packaging of electronic components, artificial body parts, grinding wheels, engine parts, and ceramic engines, to name a few.

This application relates to U.S. Pat. No. 4,569,692, entitled LOW THERMAL EXPANSIVITY AND HIGH THERMAL CONDUCTIVITY SUBSTRATE, by S. H. Butt; U.S. patent application Ser. No. 838,866, entitled CERMET SUBSTRATE WITH GLASS ADHESION COMPONENT, by D. Mahulikar (now abandoned); U.S. patent application Ser. No. 838,967, entitled CERMET SUBSTRATE WITH SPINEL ADHESION, by M. J. Pryor et al.; U.S. patent application Ser. No. 924,970, entitled ELECTRIC PACKAGING OF COMPONENTS INCORPORATING A CERAMIC-GLASS-METAL COMPOSITE, by N. N. SinghDeo et al.; U.S. patent application Ser. No. 924,959, entitled PRODUCTS FORMED OF CERAMIC-GLASS-METAL COMPOSITES, by N. N SinghDeo et al.; U.S. patent application Ser. No. 707,636, entitled PIN GRID ARRAYS, by M. J. Pryor (now abandoned) and U.S. patent application Ser. No. 922,271, entitled CERMET SUBSTRATE WITH GLASS ADHESION COMPONENT, by D. Mahulikar which is a continuation-in-part of Ser. No. 838,866 (now abandoned).

In the past, glass-ceramic composites have been formed by one-step processes into complex shapes as described in U.S. patent application Ser. No. 811,906. This technique proved effective for many applications. However, as the final product had a more complex shape, the higher pressure required to form the composite within the mold resulted in the molten glass between the ceramic particles being squeezed out and interlocking of ceramic particles. The result is a retardation of further flow so that the densification and shaping of the composite to the desired final configuration requires more pressure or may not be possible. The present invention overcomes this problem by combining metallic particles with the ceramic particles and glass to enhance the flow of the composite within the mold.

The composite may be formed of a combination of materials such that it is either electrically conductive or non-electrically conductive. Also, the coefficient of thermal expansion may be regulated in accordance with the requirements of the specific application.

A composite having a low coefficient of thermal expansion, while being non-electrically conductive, is particularly useful in the electronics industry. Presently, low expansivity materials are widely used in the microelectronic industry as substrate materials for semiconductor packages, hybrid circuit packages and chip carriers. These materials are particularly useful when the coefficient of thermal expansion (CTE) of the substrate is critical, i.e. when silicon chips or low expansivity leadless chip carriers are mounted directly to the substrate.

Alumina ceramics are presently the most widely used substrate material. There is a moderate mismatch between the coefficients of thermal expansion of alumina and the silicon chip. This mismatch does not usually generate unacceptably high stresses on a chip mounted to an alumina substrate when they are subjected to thermal cycling. This degree of CTE mismatch is usually acceptable even when the chip sizes are relatively large or when the chip is rigidly adhered to the substrate. Alumina ceramics are particularly attractive since they are less costly than most other low expansivity substrate materials. However, there are a number of drawbacks to alumina ceramics made in the conventional way such as poor tolerance control, poor thermal conductivity, i.e. in the range of about 10 to about 20 watts per meter kelvin, and manufacturing capabilities limiting alumina substrate areas to less than about 50 sq. in.

Conventional ceramic products, and ceramic substrates in particular, may be manufactured in accordance with the following procedure. Powders of alumina or other ceramic materials are mixed together with glass powders and organics. In the conventional "green tape" or "cold press" processes, the organics are two phase mixtures consisting of a solvent, such as terpineol, and a solute, such as polymethylmethacrylate. This particular solvent-solute mixture is exemplary and other organic mixtures may be used in their place. The organic mixture forms a paste or slurry when mixed with the mixture of glass and ceramic powders. The solute:solvent ratio and the type of organic mixture, is selected in accordance with the paste rheology desired for the particular application, i.e. the "green tape" or the "cold press" process.

In the green tape process, a controlled amount of slurry is placed between two sheets of plastic. The slurry, sandwiched between the plastic sheets, is passed through a rolling mill to attain a consistent thickness. The sheets of material are then cut or punched into desired shapes for firing. In the cold press process, the glass and ceramic powders are mixed with a lower percentage of solvent, as compared with the green tape process. The mixture of glass, ceramic and organics is then pressed into a desired shape and fired.

The organics, in either process, are volatilized at substantially lower temperatures than the firing or processing temperature of the ceramic bodies or ceramic substrates. The solvents usually evaporate at temperatures below about 100° C. and the solutes evaporate at temperatures below about 450° C. The loss of the solute and solvent leaves pores in the green tape or cold pressed body. At the peak firing temperatures (approximately 1600° C. for the conventional ceramics or approximately 900° C. for the low fired ceramics), the glassy phase melts, a certain amount of sintering of the alumina particles occurs, and there is a resulting densification of the bodies. The fired substrates, being devoid of any connected pores, produce a hermetic substrate that allows an extremely limited quantity of gaseous penetration ($<1\times10^{-8}$ cc He/sec). The latter characteristics of the fired substrates make them particularly suitable for fabricating hermetically sealed, semiconductor enclosures.

The densification, however, causes a great deal of shrinkage, amounting to as much as 17% in the linear dimension. It is thus unrealistic to economically produce finished parts which have better than about ±1% tolerance in the linear dimension. Therefore, dimensional tolerances for the standard fired ceramic substrates is typically quoted by ceramic manufacturers to be ±1%. Tighter dimensional tolerances are considerably more expensive so as to offset the yield loss.

The electronic industry is seeking higher levels of automation in their factories. The automatic machines are generally capable of positioning parts, such as the previously described substrates, to a much tighter tolerance than ±1% of the linear dimension of the part. In fact, the tolerance of the ceramic part is, in most cases, the limiting factor in attaining the desired level of automation.

The present invention provides a unique method of manufacturing structures of ceramic-glass-metal to their final configuration in a one-step process by conventional means at temperatures well below the firing temperature of either the conventional ceramics, i.e. about 1600° C., or even "low fired ceramics", i.e. about 900° C. The present process also imparts unique properties to the manufactured product because organics are not necessarily required in the manufacturing process.

It is a problem underlying the present invention to manufacture a ceramic-glass-metal composite whose physical characteristics can be tailored to provide specific mechanical, electrical, thermal, and chemical properties.

It is an advantage of the present invention to provide a ceramic-glass-metal composite and method of forming the composite which obviates one or more of the limitations and disadvantages of the described prior arrangements.

It is a further advantage of the present invention that a ceramic-glass-metal composite and method of forming the composite which provides a substrate having good flexure strength is provided.

It is a still further advantage of the present invention that a ceramic-glass-metal composite and method of forming the composite which can produce parts with a tight tolerance is provided.

It is another advantage of the present invention that a ceramic-glass-metal composite and method of forming the composite at a relatively low firing temperature is provided.

It is yet another advantage of the present invention that a ceramic-glass-metal composite and method of forming the composite which can be inexpensively processed is provided.

Accordingly, there has been provided a ceramic-glass-metal composite and the process of forming the composite. The unique ceramic-glass-metal composite material comprises ceramic particles, metallic particles and a glass being adherent to both the glass and the metallic particles. The glass forms a matrix with the ceramic and metallic particles dispersed throughout. The composite may be formed in a single step, by methods including hot forging and hot pressing in a mold.

The present invention particularly relates to a composite formed of a mixture of ceramic and metallic particles adhered together with a glassy phase. The composite can be formed by conventional processes such as hot forging and hot pressing into any desired shape at a processing temperature where the selected glass is preferably in the fluid condition while the metallic and ceramic particles remain in the solid condition. The resulting shaped composite may be electrically conductive or non-conductive, have a wide range of coefficients of thermal expansion, and different degrees of strength and toughness.

The invention involves mixing together appropriate proportions of at least three different types of materials to provide selected properties. One of the materials is a ceramic powder which is present in a volume percent range selected according to the desired physical property requirements such as the mechanical, electrical, thermal and chemical properties. Typically, ceramics are known for their physical characteristics including high strength, low ductility, high dielectric constant, low coefficient of thermal expansion and chemical non-reactivity. The second material is a glass which forms a matrix for binding the ceramic and metallic particles together. Since glass is relatively fragile, it is typically provided at such a proportion so as to prevent a significant reduction of the composite strength, primarily provided by the ceramic particles. The glass is selected to be chemically reactive with the ceramic particles as well as with the third material, a metal or alloy. The third material is comprised of metal or alloy particles which are dispersed throughout the composite. The metal or alloy particles enable the ceramic particles to shift position, while the composite is being pressed into a desired shape at the processing temperature, with less applied pressure as compared to a ceramic-glass slurry alone. In addition, the metal particles improve the thermal conductivity of the composite. The metal particles are preferably soft and ductile. It is believed that they tend to mold onto the adjacently disposed surfaces between adjacent ceramic particles so that the ceramic particles can slide over each other during the forming process without being damaged. It is believed that the metal particles substantially reduce the occurrence of interlocking between ceramic particles thereby reducing the pressure necessary for forming the final shapes. The resulting composite is particularly useful in that it may be readily formed by a one step process into a complex, final shape having a very tight tolerance.

The ceramic material typically comprises particles selected for their physical characteristics. The specific ceramic may be selected from the group consisting of $Al_2O_3$, SiC, BeO, $TiO_2$, $ZrO_2$, MgO, AlN, $Si_3N_4$, BN and mixtures thereof. The present invention is not limited to these ceramics and may incorporate any desired ceramic or mixture of ceramics. The ceramic particles are present in a range of from about 20 to about 80 volume percent of the final fired composite and in a preferred range of from about 40 to about 65 volume percent. The ceramic particles can have any desired shape and have an average diameter of over about 1 micron, preferably, between about 1 to about 200 microns and most preferably, between about 40 to about 100 microns. The factors considered in selecting the desired ceramic include its dielectric constant, its coefficient of thermal expansion, its strength and chemical durability.

Conventionally, ceramics have been chosen for their high temperature capabilities since their melting point is at a temperature between about 1300° to about 2500° C. However, the present invention may not require the high temperature capabilities since the ceramic particles are bonded together in a glassy matrix which may have a relatively low softening temperature as compared to that of the ceramic. It is also within the terms of present invention to choose glasses which can be frabricated into components that are stable at very high temperatures.

A second component of the composite comprises a glassy phase having any desired composition in accordance with the properties required by the final composite. The glassy phase functions to bind the ceramic and metallic particles together within a matrix of the glass. An important characteristic is that the glass preferably is chemically reactive with both the ceramic and metallic components. Also, it may be important that the glass has physical characteristics such as good chemical durability, high strength, an acceptable dielectric constant, and a softening point in a selected temperature range. Suitable glasses may be selected from the group consisting of silicate, borosilicate, phosphate, zinc-borosilicate, soda-lime-silica, lead-silicate, lead-zinc-borate glasses, however, any desired glass may be utilized. They may include phosphate glass systems having high coefficients of thermal expansion and relatively low temperature softening points. In addition, a vitreous or devitrified glass may be selected.

A preferred example of a useful glass which provides thermosetting properties suitable for application in an electronic environment is a devitrified, solder glass. This glass is a $PbO-ZnO-B_2O_3$ type glass and has a nominal composition of about 10 wt. % B, 0.025 wt. % A, 8.5 wt. % Si, 0.04 wt. % Ti, 0.01 wt. % Fe, 8.5 wt. % Zn, 12.5 wt. % Zr, 0.25 wt. % Hf, 2.0 wt. % Ba and the balance Pb. All elements are reported as wt. % of corresponding oxide. After the glass is liquid, it is held at a temperature of about 500° C. for about 10 minutes. The glass, upon solidification, then devitrifies. At that point, it will not remelt until it reaches a temperature of about 650° C. The glass is present in a range of from about 15 to about 50 volume percent of the fired composite and in a preferred range of from about 20 to about 40 volume percent. The glass is preferably selected with a softening temperature of from about 300° to about 1300° C. The processing temperature is selected so that the glass is at least above its softening point and preferably is in the liquid state.

A thermosetting composite may be formed by mixing ceramic and metal particles with a glass that devitrifies above a certain temperature. First, the composite is preferably formed at a processing temperature where the glass is in a liquid condition. The composite may then be held in an oven at approximately the processing temperature for a sufficient period so that it has a devitrified structure when it solidifies. When the glass is in the crystalline state, it is usually much stronger than in the vitreous state. A composite of this nature, i.e. ceramic and metal particles mixed with a devitrified glass, may be characterized as a thermosetting material. The latter characteristic is imparted because the remelting temperature is considerably higher than the original processing temperature.

For example, a devitrifiable solder glass, CVIII ™ manufactured by Owens Illinois Co., becomes liquid at a processing temperature of about 470° C. This glass as previously described is a $PbO-ZnO-B_2O_3$ type glass and has a nominal composition of about 10 wt. % B, 0.025 wt. % A, 8.5 wt. % Si, 0.04 wt. % Ti, 0.01 wt. % Fe, 8.5 wt. % Zn, 12.5 wt. % Zr, 0.25 wt. % Hf, 2.0 wt. % Ba and the balance Pb. All elements are reported as wt. % of corresponding oxide. After the glass is liquid, it is held at a temperature of about 500° C. for about 10 minutes so that upon solidification it has a devitrified structure. At that point, it will not remelt until it reaches a temperature of about 650° C. The thermosetting characteristics of the devitrified glasses are particularly advantageous because they allow the final product to be used in a higher temperature environment than the original processing temperature.

The third component of the composite comprises metallic particles which preferably are ductile at the processing temperature. The metallic particles are provided for their ability to reduce significantly the pressure necessary to densify the final composite product. It is believed that they mold about the surfaces of the ceramic particles when they are pressed between the ceramic particles during the processing procedures, thereby reducing or eliminating interlocking of the ceramic particles so as to reduce processing pressures. For example, the usual processing includes heating the mixture of ceramic particles with the metallic particles and the glass to the processing temperature where the metal particles are soft and ductile but not molten. The resulting composite slurry may be formed, i.e. in a mold. As the ceramic-glass-metal slurry flows into the shape of the mold, the ceramic particles are pressed against each other. The glassy phase is squeezed out from between adjacent ceramic particles providing points of contact. Without the presence of the metallic particles, the ceramic particles would remain in contact and could lock in position thereby retarding the ability of the slurry to flow. The ease of flowability is required for densification and shaping of the composite to the desired final configuration. Any loss of flowability becomes increasingly significant as the final shape becomes more complex.

A unique aspect of the present invention is the addition of metallic particles into the composite to significantly affect the flowability of the composite slurry. The metallic particles act sort of as a lubricant to enable the ceramic particles to slide over each other. It is believed that some of the metallic particles move into the interstices between adjacent ceramic particles and mold onto the ceramic particles at the points of contact which could interlock. It is believed that the metallic particles, being squeezed by the ceramic particles moving towards each other, adhere to the ceramic particles and then deform. This deformation enables the slurry containing the ceramic particles to move and flow, i.e. in a mold, while preventing damage to the ceramic particles.

The metallic particles may be constituted of any metal or alloy which does not melt at the processing temperature of the composite. Preferably, the metals and alloys are selected from the group consisting of aluminum, copper, iron, silver, gold, stainless steel and alloys thereof. Preferably, the selected metals and alloys are ductile at the processing temperature. Since any metal or alloy is ductile slightly below its melting temperature and below its solidus, respectively, a suitably selected processing temperature enables the use of any metal or alloy which will be ductile at the latter temperature. In the case where the metal or alloy is not ductile enough at the processing temperature, added pressure may be applied during the forming process to provide the required deformation. The metal or metal alloy particles preferably have an average diameter between about, 0.01 to about 50 microns.

The final, fired composite may either contain the metallic particles dispersed continuously or discontinuously throughout the composite. Even in the case where the metallic particles are dispersed continuously, they do not form a matrix and are primarily subject to localized sintering. When the particles are dispersed continuously, the product would be classified as electrically conductive and when the particles are dispersed discontinuously the product would typically be classified as an insulator.

The metallic particles are present in the composite in an effective amount up to about 45 vol. % of the fired composite to enhance the flow characteristics of the composite at the processing temperature. Preferably, the metallic particles make up from about 5 to about 45 vol. % of the composite.

For applications where the composite is preferably classified as an insulator such as for electronic packaging components, the metallic particles are preferably provided in a volume percent so that they are discontinuously dispersed throughout the fired composite. Preferably, the metal or metal alloy particles in this instance make up less than about 25 volume percent of the final, fired composite. More preferably, the metal particles make up less than about 15 volume percent of the fired composite. Limiting the volume percent of metallic particles within these ranges is believed to prevent the formation of a continuous metal path in the final, fired composite.

The final composite, even with discontinuously dispersed metallic particles, exhibits improved thermal conductivity as compared with a composite formed with only ceramic particles bonded together with a glassy matrix. It is particularly surprising that the final composite having dispersed metallic particles has increased thermal conductivity since there is no corresponding increase in electrical conductivity. The reason for this unusual characteristic is not fully understood.

For application where the composite is preferably classified as electrically conductive, the metallic particles are preferably provided in a volume percent so that they are continuously dispersed throughout the fired composite. Preferably, the metal or metal alloy particles in this instance make up more than about 25 volume percent of the final, fired composite. More preferably, the metal or metal alloy particles make up from about 30 to about 45 volume percent of the fired composite. Limiting the volume percent of the metallic particles within these ranges is believed to promote the formation of a continuous metal path in the final, fired composite thereby providing good electrical conductivity as well as thermal conductivity. Such an electrically conductive composite is believed to have wide application in areas outside the electronic packaging field such as in engineered composites and electronic composites where electrical conductivity is desired.

The process of forming the composite of the present invention includes providing three primary components; ceramic particles, metallic particles and a glass. The process may be accomplished by different techniques depending on the specific materials selected. For example, the ceramic particles may first be mixed with relatively ductile metal particles. Next, glass particles for bonding the ceramic particles together are added to the mixture. The mixture is heated to the processing temperature preferably corresponding to the temperature at which the glass particles are liquid and at least to their softening temperature. This preferably provides a semi-solid slurry of molten glass with solid metal and ceramic particles dispersed therein. Then, the composite preferably as a semi-solid slurry can be formed by conventional processes such as hot forging or hot pressing in a mold to any desired shape. With hot pressing, the mixture is preferably compacted at a pressure of from about 500 pounds per square inch (psi) to about $300 \times 10^3$ psi The lowest usable pressure is believed to be that which enables the metallic particles, adhered between adjacent ceramic particles, to deform. This depends on the ductility of the metal or alloy at the processing temperature. In the event that the metal is not ductile enough at the processing temperature, a higher pressure may be used to deform the metal particles.

Finally, the mixture is cooled to solidify the glass and bind the composite into a final devitrified shape. A conventional parting agent, such as boron nitride, may be provided on the mold walls to enhance the removal of the pressed product from the mold. Preferably, the parting agent does not stick to either the mold walls or the pressed body. However, the primary consideration is that the parting agent does not stick to the mold walls. An important advantage of the present invention is that the pressed composite is very dense and has a final shape that very closely corresponds to that of the mold.

The present invention can produce parts with much tighter tolerance, and a more complex shape than ceramic manufacturing processes currently available in the industry. This significant advantage is primarily due to the following reasons. Firstly, the starting materials do not necessarily contain any constituents, such as organics, which are lost during the actual process of fabrication. These losses can result in undue shrinkage. Secondly, the metal particles enable the ceramic particles to better flow over each other during processing. Another important advantage is that the firing temperature may be substantially lower than the range of temperatures at which ceramic materials are now fired. Processing at a lower temperature inherently decreases the processing cost as compared to any known process.

The fabrication process may include conventional steps including hot pressing and hot forging. Hot pressing can be carried out directly on the mixture of powders or on cold compacts. Depending on the glass, however, the hot pressing may require oxidizing atmospheres. For example, a solder glass such as $PbO-ZnO-B_2O_3$ requires an oxidizing atmosphere to prevent a change in the state of the glass.

Additional improvements in both thermal and mechanical properties can be obtained by using devitrified glasses in the composite. For electronic packaging, a devitrified glass enables the package to be formed at a significantly lower temperature than the temperature at which the package will operate.

An exemplary process follows.

About 45 vol. % of a devitrifying glass (Owens Illinois CVIII) in fine particulate form ($-325$,90% mesh) was mixed with about 45 vol. % of fine particulate $Al_2O_3$ ($-120$ mesh) and about 10 vol. % of fine atomized aluminum metal powder ($-325$ mesh). The resulting mixture was cold compacted at about $50 \times 10^3$ psi. The cold compacts were then hot pressed into $1\frac{1}{4}''$ dia. 0.1" thick discs at a temperature of about 470° C. and under a pressure of about $25 \times 10^3$ psi The discs were then placed in an oven and kept at a temperature of about 500° C. for about 10 minutes so that the final structure was devitrified.

The resultant discs had a density of higher than about 99% of theoretical achievable density. Other physical characteristics of the composite discs include a gas leak rate of about $8 \times 10^{-8}$ atm cc/sec., a thermal expansion of about $85 \times 10^{-7}$ in/in/°C. and a thermal conductivity of about 0.02 cal/cm °C. The sample discs did not show any electrical conductivity reading on an eddy current loss probe.

An example of a ceramic-glass-metal composite formed of a vitreous glass follows.

About 45 vol. % of a vitreous glass (Corning 7052) in a fine particulate form (−325, 90% mesh) can be mixed with about 45 vol. % of fine particulate Al$_2$O$_3$ (−120 mesh) and about 10 vol. % of fine atomized iron metal powder (−325 mesh). The resulting mixture can be cold compacted at about $50 \times 10^3$ psi. The cold compacts can then be hot pressed into discs at a temperature of about 1220° C. and under a pressure of about $25 \times 10^3$ psi pressure. The discs can then be solidified into final structures that are vitreous. The resultant discs are thought to be very dense, have a thermal expansion of about $70 \times 10^{-7}$ in./in./°C. and be an insulator.

The ceramic-glass-metal composite may also be constituted so as to be electrically conductive. An example of this type of structure is provided. About 15 vol. % of a vitreous glass (Corning 7052) in fine, particulate form (−325, 90% mesh) may be mixed with about 40 vol. % of fine atomized iron metal powder (−325 mesh) and the remainder of fine particulate Al$_2$O$_3$ (−120 mesh). The resulting mixture can be cold compacted at about $50 \times 10^3$ psi. The cold compacts can then be hot pressed into discs at a temperature of about 1220° C. and under a pressure of about $25 \times 10^3$ psi pressure. The discs can then be solidified into final structures that are vitreous. The resultant discs are thought to be very dense, have a thermal expansion of about $86 \times 10^{-7}$ in./in./°C.

For the purpose of this invention, a final, fired composite is defined as the composite after densification at the processing temperature. Discontinuously dispersed means that the particles are not generally interconnected so as to provide electrical conductivity. Continuously dispersed means that the particles are generally interconnected to provide electrical conductivity.

Although the present invention is described in terms of hot pressure forming, it is also within the terms of the present invention to form the ceramic-glass-metal composite using other techniques, such as those employed in glass manufacture, including casting, blow casting and blowing.

The patent and patent applications set forth in this application are intended to be incorporated in their entireties by reference herein.

It is apparent that there has been provided in accordance with this invention a ceramic-glass-metal composite which satisfies the objects, means and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications and all variations as fall within the spirit and broad scope of the appended claims.

We claim:

1. A ceramic-glass metal composite, comprising:
   from about 5 to about 45 volume % of metallic particles for enhancing the flow characteristics of said composite;
   from about 15 to about 50 volume % of a glass for adhering said composite together;
   the balance essentially ceramic particles;
   said metallic particles substantially smaller than said glass or ceramic particles; and
   said composite having a structure comprising substantially a matrix of said glass with said ceramic and metallic particles dispersed therein.

2. The composite of claim 1 including said ceramic particles comprising from about 20 to about 80 vol. percent of said composite.

3. The composite of claim 2 wherein said ceramic particles comprises from about 40 to about 65 vol. percent of said composite.

4. The composite of claim 2 including said ceramic particles being over about 1 micron in average diameter.

5. The composite of claim 4 including said ceramic particles being from about 1 to about 200 microns in average diameter.

6. The composite of claim 4 including said ceramic particles being selected from the group consisting of Al$_2$O$_3$, SiC, BeO, TiO$_2$, ZrO$_2$, MgO, AlN, Si$_3$N$_4$, BN and mixtures thereof.

7. The composite of claims 1, 3 or 4 including said metallic particles being greater than about 0.01 micron in average diameter.

8. The composite of claim 4 including said metallic particles being from about 0.01 to about 50 microns in average diameter.

9. The composite of claims 1, 4 or 8 wherein said metallic particles are discontinuously dispersed throughout said composite.

10. The composite of claims 1, 4 or 8 wherein said metallic particles are continuously dispersed throughout said composite.

11. The composite of claim 8 wherein said metallic particles comprise effective amount up to less than about 25 volume percent of said composite and said metallic particles are discontinuously dispersed throughout said composite for providing electrically an insulating composite.

12. The composite of claim 8 wherein said metallic particles comprise an effective amount of from about 30 volume percent of said composite to about 45 volume percent and said metallic particles are continuously dispersed throughout said composite for providing an electrically conductive composite.

13. The composite of claim 6 wherein said metallic particles are selected from the group consisting of aluminum, copper, iron, silver, gold, stainless steel and alloys thereof.

14. The composite of claims 11, 12 or 13 further including said glass being vitreous.

15. The composite of claims 11, 12 or 13 further including said glass being a devitrified glass.

16. The composite of claims 11, 12 or 13 including said glass being selected from the group consisting of silicate, borosilicate, phosphate, zinc-borosilicate, soda-lime-silica, lead-silicate and lead-zinc-borate glasses.

17. The composite of claims 11, 12 or 13 wherein said glass comprises from about 20 to about 40 volume percent.

18. The process of forming a ceramic-glass-metal composite, comprising the steps of:
    providing a mixture comprising:
    from about 5 to about 45 volume % of metallic particles for enhancing the flow characteristics of said composite; from about 15 to about 50 volume % of glass particles for adhering said composite together; and the balance of essentially ceramic particles; said metallic particles being substantially smaller than said ceramic or glass particles;

heating said mixture to a processing temperature, said processing temperature being selected so as to be above the glass softening point of said glass particles and below the melting point of said metallic particles;

pressing said mixture at said processing temperature into a desired shape; and solidifying said glass to form a composite structure comprising substantially a matrix of said glass with said ceramic and metallic particles dispersed therein.

19. The process of claim 18 including the step of selecting said ceramic particles to comprise from about 20 to about 80 vol. percent of said composite.

20. The process of claim 19 including the step of selecting said ceramic particles to comprise from about 40 to about 65 vol. percent of said composite.

21. The process of claim 19 including the step of selecting said ceramic particles having an average diameter of greater than about 1 micron.

22. The process of claim 21 including the step of selecting said ceramic particles having an average diameter of from about 1 to about 200 microns.

23. The process of claim 22 including the step of selecting said ceramic particles from the group of $Al_2O_3$, SiC, BeO, $TiO_2$, $ZrO_2$, MgO, AlN, $Si_3N_4$, BN and mixtures thereof.

24. The process of claims 18, 20 or 21 including the step of selecting said metallic particles having an average diameter of greater than about 0.01 micron.

25. The process of claim 21 including the step of selecting said metallic particles having an average diameter of from about 0.01 to about 50 microns.

26. The process of claims 18, 21 or 23 wherein said metallic particles are discontinuously dispersed throughout said composite.

27. The process of claims 18, 21 or 25 wherein said metallic particles are continuously dispersed throughout said composite.

28. The process of claim 25 including the step of selecting said metallic particles to comprise an effective amount up to less than about 25 wt. percent of said composite and dispersed discontinuously throughout said composite for providing an electrically insulating composite.

29. The process of claim 25 including the step of selecting said metallic particles to comprise an effective amount of about 30 volume percent to about 45 volume percent of said composite and dispersed continuously throughout said composite for providing an electrically conductive composite.

30. The process of claim 23 further including the step of selecting the metallic particles from the group consisting of aluminum, copper, iron, silver, gold, stainless steel and alloys thereof.

31. The process of claims 28, 29 or 30 further including the step of selecting a vitreous glass.

32. The process of claims 28, 29 or 30 further including the step of selecting a devitrified glass.

33. The process of claims 28, 29 or 30 further including the step of selecting the glass from the group consisting of silicate, borosilicate, phosphate, zinc-borosilicate, soda-lime-silica, lead-silicate and lead-zinc-borate glasses.

34. The process of claims 28, 29 or 30 further including the step of selecting said glass to comprise from about 20 to about 40 volume percent.

* * * * *